(12) United States Patent
Rohinsky et al.

(10) Patent No.: US 9,271,911 B2
(45) Date of Patent: Mar. 1, 2016

(54) QUARTERNARY AMINE SURFACTANT CLEANER

(71) Applicant: OAP Cleaner LLC, Hewlett, NY (US)

(72) Inventors: Michael Rohinsky, Far Rockaway, NY (US); Glen Brezius, Augusta, GA (US)

(*) Notice: Subject to any disclaimer, the term of this patent is extended or adjusted under 35 U.S.C. 154(b) by 0 days.

(21) Appl. No.: 14/079,816

(22) Filed: Nov. 14, 2013

(65) Prior Publication Data

US 2014/0171350 A1 Jun. 19, 2014

Related U.S. Application Data

(60) Provisional application No. 61/738,377, filed on Dec. 17, 2012.

(51) Int. Cl.
| | | |
|---|---|---|
| *C11D 3/48* | (2006.01) | |
| *C11D 1/72* | (2006.01) | |
| *C11D 1/835* | (2006.01) | |
| *C11D 1/62* | (2006.01) | |
| *A61K 8/41* | (2006.01) | |
| *A61Q 11/02* | (2006.01) | |
| *A61K 8/34* | (2006.01) | |
| *A61K 8/49* | (2006.01) | |
| *A61K 8/92* | (2006.01) | |
| *A61K 8/97* | (2006.01) | |

(52) U.S. Cl.
CPC .............. *A61K 8/416* (2013.01); *A61K 8/347* (2013.01); *A61K 8/49* (2013.01); *A61K 8/922* (2013.01); *A61K 8/97* (2013.01); *A61Q 11/02* (2013.01)

(58) Field of Classification Search
CPC ........ C11D 3/0052; C11D 3/48; C11D 3/485; C11D 1/72; C11D 1/835; C11D 1/62
See application file for complete search history.

(56) References Cited

U.S. PATENT DOCUMENTS

2012/0295940 A1* 11/2012 Sookram et al. .............. 514/358

* cited by examiner

*Primary Examiner* — Charles Boyer
(74) *Attorney, Agent, or Firm* — Power Del Valle LLP; Marguerite Del Valle

(57) ABSTRACT

A composition for cleaning and sanitizing dental appliances and dentures having at least one of anti-viral, anti-fungal, antibacterial, germicidal, and anti-microbial properties and comprising (a) a surfactant system having a quaternary amine as a first component and a nonionic surfactant as a second component, (b) peppermint oil, (c) a quaternary salt additive, (d) propolis resin extract, (e) antibiotic additive, and (f) Triclosan.

5 Claims, No Drawings

QUARTERNARY AMINE SURFACTANT CLEANER

This application claims priority from provisional patent application 61/738377, filed Dec. 17, 2012.

The present invention relates to a liquid cleanser, useful for dental appliances and dentures, composed of (a) a surfactant system having a quaternary amine as a first component and a nonionic surfactant as a second component and (b) peppermint oil, and optionally including a quaternary salt additive, propolis resin extract, an antibiotic additive, and triclosan.

BACKGROUND OF THE INVENTION

The prior art discloses various compositions designed to remove plaque and scale buildup on dental appliances and dentures. See, e.g., U.S. Pat. No. 5,047,163 disclosing bleach precursors with sulfonimines; U.S. Pat. No. 5,045,223 disclosing N-sulfonyloxaridines as bleaching compounds; and U.S. Pat. No. 5,041,236 disclosing antimicrobial methods and compositions employing lysozymes and endoglycosidases. There also numerous references using perborate, carbonate, bicarbonate, and phosphate salts to generate effervescence. See, e.g, U.S. Pat. No. 4,405,486.

The resin base utilized by nearly all removable orthodontic appliances exhibits a certain degree of porosity which can harbor a vast accumulation of harmful pathogens and plaque. This increase in microorganisms can provide an increased risk for many serious ailments, including heart disease and diabetes. While prior art cleaning solutions and devices may remove some odors and stains and large particles from dental appliances, they do not provide protection against bacteria, viruses, and germs that reside and multiply on the appliance, as well as in the container in which it is stored. Moreover, some prior art cleaning solutions are known to discolor and stain appliances or to leave an unpleasant odor or taste on the appliance.

BRIEF SUMMARY OF THE INVENTION

The present invention is a dental appliance cleaner that also has at least one of anti-viral, anti-fungal, antibacterial, germicidal, and anti-microbial properties. The preferred embodiment of this invention is composed of (a) a surfactant system having a quaternary amine as a first component and a nonionic surfactant as a second component, (b) peppermint oil, and at least one of the following further components: a quaternary salt additive, propolis resin extract, (e) an antibiotic additive, and (f) Triclosan.

DETAILED DESCRIPTION OF THE INVENTION

The inventive formulation calls for the use of two different surfactants. A surfactant acts not only as a detergent but also as a wetting agent, which helps the cleaner to spread over the surface and allows the other components easier access to microscopic cracks and crevices. The surfactants act as soaps primarily, lifting oil-soluble dirt and grime away from a surface, but the surfactants of the present invention also have synergistic effects with other molecules in the formulation which boost the antimicrobial behavior.

The first surfactant in this formulation is a quaternary amine-containing ionic surfactant which has a positively charged ammonium cation along with a hydrophobic "tail" that resembles a lipid.

The virucidal activity of soaps with amine "heads" is dependent on the acidity of the solution. The present formulation uses an acidity stabilizer to ensure the pH value remains in the desired range (centered on 6.5) which maximizes the increased antiviral behavior.

The first component is in the form $R-C(O)-O^-N^+R_2R_3R_4R_5$, where R is chosen from a $C_{1-24}$ alkyl, $C_{6-20}$ aryl, or $C_{3-20}$ cycloalkane. $R_2$, $R_3$, $R_4$ and $R_5$ can be independently chosen from a mixture of H, $C_{1-20}$ alkyl, $C_{6-20}$ aryl, $C_{3-20}$ cycloalkane, or an oligo(ethylene glycol) group of the form $-(CH_2CH_2O)_nR_6$, where n is between 2 and 24 and $R_6$ is either H or an alkyl group.

The inventive formulation also employs a nonionic surfactant, having antimicrobial behavior, which acts in synergy with quaternary amine salts. Accordingly, Triton X-100 is added as the second surfactant. Triton X-100 is a very viscous material, but it is freely soluble in water as are any of the possible structures for the first surfactant.

Regardless of the structure of the first surfactant, the surfactant system comprises 1-20% total percentage loading (by weight), with a total of 10% being ideal, e.g., 5% of the first surfactant and 5% of the second surfactant or some other combination within this parameter.

Peppermint oil is added in amounts of about 0.5-2% by weight. Peppermint oil is a very complex mixture, being a plant extract, but its primary component is menthol, which makes up 25-50% of the oil.

A quaternary amine salt, having the structure $N^+R_1R_2R_3R_4$, where $R_1$, $R_2$, $R_3$ and $R_4$ can be independently chosen from a mixture of H, $C_{1-20}$ alkyl, $C^{6-20}$ aryl, $C_{3-20}$ cycloalkane, or an oligo(ethylene glycol) group of the form $-(CH_2CH_2O)_nR_5$, where n is between 2 and 24 and $R_5$ is either H or an alkyl group, is added in amounts of 0.1% to 15% by weight, with 7.5% being ideal. Some examples of the cation would be cetrimide, benzalkonium, dofanium, benzethonium, methylbenzethonium, cetylpyridinium, cetrimonium, tetraethylammonium, idodecyldimethylammonium, and combinations thereof.

A further component of the inventive formulation is propolis. It is a resin, a relatively inexpensive natural product that comes from bees. It is a mixture of phenolic compounds, terpenoids, aromatic and aliphatic acids as well as flavonoid compounds. All of these components work in synergy to produce a very powerful antimicrobial agent. A number of studies have found that samples of propolis have strong activity against gram-positive and gram-negative as well as fungi. Depending on its source, propolis resin can be dark in hue, but some regions (it depends on where the bees are from) produce propolis with a whitish hue. In any case, in this formulation, this propolis resin additive is added in a 0.1%-5% range (by weight), with 2.5% being ideal, so coloration should be minimal. Also, the additive used for this formulation is the ethanol extract of propolis resin, produced by exhaustive (Soxhlet-type) extraction of propolis resin with ethanol followed by removal of ethanol solvent. This will leave most of the tar-like, highly colored materials in the Soxhlet filter and produces a colorless extract.

An antibiotic additive is chosen from cephalosporin, cefepime, cephaloridine, or a mixture thereof, and added in 0.1% to 1.0% (by volume), with 0.5% being ideal.

Triclosan, an antibacterial compound, is added in the range of 1-5%; 2.5% is the amount contained in the preferred embodiment. While triclosan is largely hydrophobic, the surfactants present in the formulation will act as emulsifiers and bring the triclosan into solution.

The solution is thickened to the desired viscosity, 25 k-100 k cP. This is accomplished by the addition of a thickening agent, selected from viscose, poly(vinyl) alcohol, partially hydrolyzed poly(vinyl acetate), xanthan gum, sodium alginate, hydroxypropyl starch, gelatin, pectin, agar, arabic gum, dextrin, maltodextrin, chitosan, polyethylene glycol, and guar gum, and combinations thereof. The preferred embodiment is thickened with hydroxypropyl starch. The exact percentage loading needed for the formulation depends on the structures/percentage loadings chosen up to this point.

The final additive is an acidity regulator to maintain the formulation in the range of pH=6.25 to 6.75; the preferred embodiment having a 6.5 pH. To this end, an organic acid or organic acid salt such as benzoic acid/sodium benzoate (or if necessary, a stronger base/acid such as dilute hydrochloric acid or dilute sodium hydroxide) is added to adjust the pH of the final solution. Sodium benzoate would also serve to act as a preservative for the storage of the cleanser over time, so it is advantageous to add it in a 0.1% loading if another acidity regulator is chosen.

The general formulation of the present invention is:
1%-20% of a combination of surfactant 1 plus surfactant 2
0.5%-2% of peppermint oil
0.1%-15% of quaternary salt additive
0.1-5% of propolis resin extract
0.1-1.0% of antibiotic additive
1%-5% of Triclosan These materials are dissolved up to 50% (by weight) of water. Deionized/distilled water is appropriate, although not strictly necessary as trace ions are not especially problematic. The exception would be city water from areas with heavy chlorination, as those could affect some of the more delicate molecular components.

All of the components go into solution with stirring. The viscosity is measured using a standard Ostwald-type viscometer. The thickener additive and additional water are added together to make a total of 100% (with viscosity measurements along the way) so that the final product has the correct thickness.

The pH is then adjusted to the desired range using the acidity regulator additive.

The specific protocol for preparing an embodiment of the invention is as follows:

The following materials are added to a 250 round-bottom flask equipped with a stir bar:
10 g triethyldodedanoyl ammonium chloride
10 g Triton X-100
2 g peppermint oil
7.5 g benzyldimethyldecyl ammonium chloride
2.5 g propolis resin extract (previously prepared using standard Soxhlet techniques)
0.5 g cephalosporin
2.5 g triclosan.

Then, 16 milliliters of distilled water are added and the contents of the flask are stirred. There may be a mild exotherm (heating) upon dissolution of the salts, which is controlled by placing the round-bottom flask in an ice bath. Once all the materials are dissolved (several minutes stirring at room temperature), the viscosity is checked. At this point there are 50 grams of material in the flask. Water and hydroxypropyl starch are added alternatively (with stirring) in amounts necessary to reach 100 total grams of material with the correct viscosity. Finally, the pH is checked and adjusted to 6.75 with the addition of either benzoic acid or a few drops of concentrated HCl (if the current pH is>6.75), or sodium benzoate or a few drops of 25% NaOH solution (if the current pH is<6.75). The solution is stirred for a few moments longer, using a top-down stirrer (mechanically driven, rather than a simple stir plate), to ensure the solution is well mixed.

The inventive formulation is applied to a dental appliance and left on for at least one minute at which point the appliance will be sanitized.

The thickening agent can be omitted if it is desired to employ the product as a spray. Moreover, the peppermint oil may be eliminated as well to yield a product which is odorless.

The invention may be embodied in other forms or carried out in other ways without departing from the spirit or essential characteristics thereof. The present disclosure is to be considered as illustrative and not restrictive, the scope of the invention being indicated by the appended claims. All modification that come within the meaning and range of equivalency are intended to be embraced herein.

The invention claimed is:

1. A cleaning solution comprising:
   a. an antimicrobial surfactant system present in amounts of 1 to 20% by weight comprising a combination of:
      i. a quaternary amine surfactant having biocidal properties selected from a group having the structure R—C(O)—O$^-$N$^+$R$_2$R$_3$R$_4$R$_5$, where R is chosen from a C$_{1-24}$ alkyl, C$_{6-20}$ aryl, or C$_{3-20}$ cycloalkane, R$_2$, R$_3$, R$_4$ and R$_5$ are chosen from a mixture of H, C$_{1-20}$ alkyl, C$_{6-20}$ aryl, C$_{3-20}$ cycloalkane, or a first oligo-ethylene glycol group of the structure —(CH$_2$CH$_2$O)$_n$R$_6$, where n is between 2 and 24 and R$_6$ is either H or an alkyl group, and
      ii. a non-ionic surfactant having a second oligo-ethylene glycol chain; and
   b. a first additional antibacterial, antiviral, or antifungal component present in amounts of 0.5-2% by weight wherein the first additional antibacterial, antiviral, or antifungal component is peppermint oil.

2. A cleaning solution of comprising:
   a. an antimicrobial surfactant system present in amounts of 1 to 20% by weight comprising a combination of:
      i. a quaternary amine surfactant having biocidal properties selected from a group having the structure R—C(O)—O$^-$N$^+$R$_2$R$_3$R$_4$R$_5$, where R is chosen from a C$_{1-24}$ alkyl, C$_{6-20}$ aryl, or C$_{3-20}$ cycloalkane, R$_2$, R$_3$, R$_4$ and R$_5$ are chosen from a mixture of H, C$_{1-20}$ alkyl, C$_{6-20}$ aryl, C$_{3-20}$ cycloalkane, or a first oligo-ethylene glycol group of the structure —(CH$_2$CH$_2$O)$_n$R$_6$, where n is between 2 and 24 and R$_6$ is either H or an alkyl group, and
      ii. a non-ionic surfactant having a second oligo-ethylene glycol chain; and
   b. a first additional antibacterial, antiviral, or antifungal component present in amounts of 0.5-2% by weight; and
   c. an antimicrobial component present in amounts of 0.1 to 5% wherein the antimicrobial component is selected from a group including propolis resin extract.

3. A cleaning solution comprising:
   a. an antimicrobial surfactant system present in amounts of 1 to 20% by weight comprising a combination of:
      i. a quaternary amine surfactant having biocidal properties selected from a group having the structure R—C(O)—O$^-$N$^+$R$_2$R$_3$R$_4$R$_5$, where R is chosen from a C$_{1-24}$ alkyl, C$_{6-20}$ aryl, or C$_{3-20}$ cycloalkane, R$_2$, R$_3$, R$_4$ and R$_5$ are chosen from a mixture of H, C$_{1-20}$ alkyl, C$_{6-20}$ aryl, C$_{3-20}$ cycloalkane, or a first oligo-ethylene glycol group of the structure —(CH$_2$CH$_2$O)$_n$R$_6$, where n is between 2 and 24 and R$_6$ is either H or an alkyl group, and ii. a non-ionic surfactant having a second oligo-ethylene glycol chain;
b. a first additional antibacterial, antiviral, or antifungal component present in amounts of 0.5-2% by weight; and
c an antibiotic additive in amounts of 0.1 to 1.0% wherein the antibiotic additive is selected from the group consisting of cephalosporin, cefepime, cephaloridine, or a mixture thereof.

4. A cleaning solution of comprising:
a. an antimicrobial surfactant system present in amounts of 1 to 20% by weight comprising a combination of:
   i. a quaternary amine surfactant having biocidal properties selected from a group having the structure R—C(O)—O$^-$N$^+$R$_2$R$_3$R$_4$R$_5$, where R is chosen from a C$_{1-24}$ alkyl, C$_{6-20}$ aryl, or C$_{3-20}$ cycloalkane, R$_2$, R$_3$, R$_4$ and R$_5$ are chosen from a mixture of H, C$_{1-20}$ alkyl, C$_{6-20}$ aryl, C$_{3-20}$ cycloalkane, or a first oligo-ethylene glycol group of the structure —(CH$_2$CH$_2$O)$_n$R$_6$, where n is between 2 and 24 and R$_6$ is either H or an alkyl group, and
   ii. a non-ionic surfactant having a second oligo-ethylene glycol chain; and
b. a first additional antibacterial, antiviral, or antifungal component present in amounts of 0.5-2% by weight; and
c. an antibacterial component in amounts of 0.1 to 0.45% by weight wherein the antibacterial component is Triclosan.

5. A dental appliance cleaning solution comprising:
a. an antimicrobial surfactant system present as 10% by weight comprising a combination of:
   i. a quaternary amine surfactant having biocidal properties selected from a group having the structure R—C(O)—O$^-$N$^+$R$_2$R$_3$R$_4$R$_5$, where R is chosen from a C$_{1-24}$ alkyl, C$_{6-20}$ aryl, or C$_{3-20}$ cyclohexane, R$_2$, R$_3$, R$_4$ and R$_5$ are chosen from a mixture of H, C$_{1-20}$ alkyl, C$_{6-20}$ aryl, C$_{3-20}$ cycloalkane, or a first oligo-ethylene glycol group of the structure —(CH$_2$CH$_2$O)$_n$R$_6$, where n is between 2 and 24 and R$_6$ is either H or an alkyl group, and
   ii. Triton X-100;
b. peppermint oil present as 0.5 to 2% by weight;
c. a quaternary salt additive, present as 7.5% by weight, selected from the group having the structure N$^+$R$_1$R$_2$R$_3$R$_4$, where R$_1$, R$_2$, R$_3$ and R$_4$ are chosen from a mixture of H, C$_{1-20}$ alkyl, C$_{6-20}$ aryl, C$_{3-20}$ cycloalkane, or an oligo-ethylene glycol group of the form —(CH$_2$CH$_2$O)$_n$R$_5$, where n is between 2 and 24 and R$_5$ is either H or an alkyl group;
d. propolis resin extract present as 2.5% by weight;
e. an antibiotic additive selected from the group consisting of cephalosporin, cefepime, cephaloridine, or a mixture thereof;
f. Triclosan present as 2.5% by weight.

* * * * *